ALMOND TREE
Filed Jan. 26, 1972 3 Sheets-Sheet 1
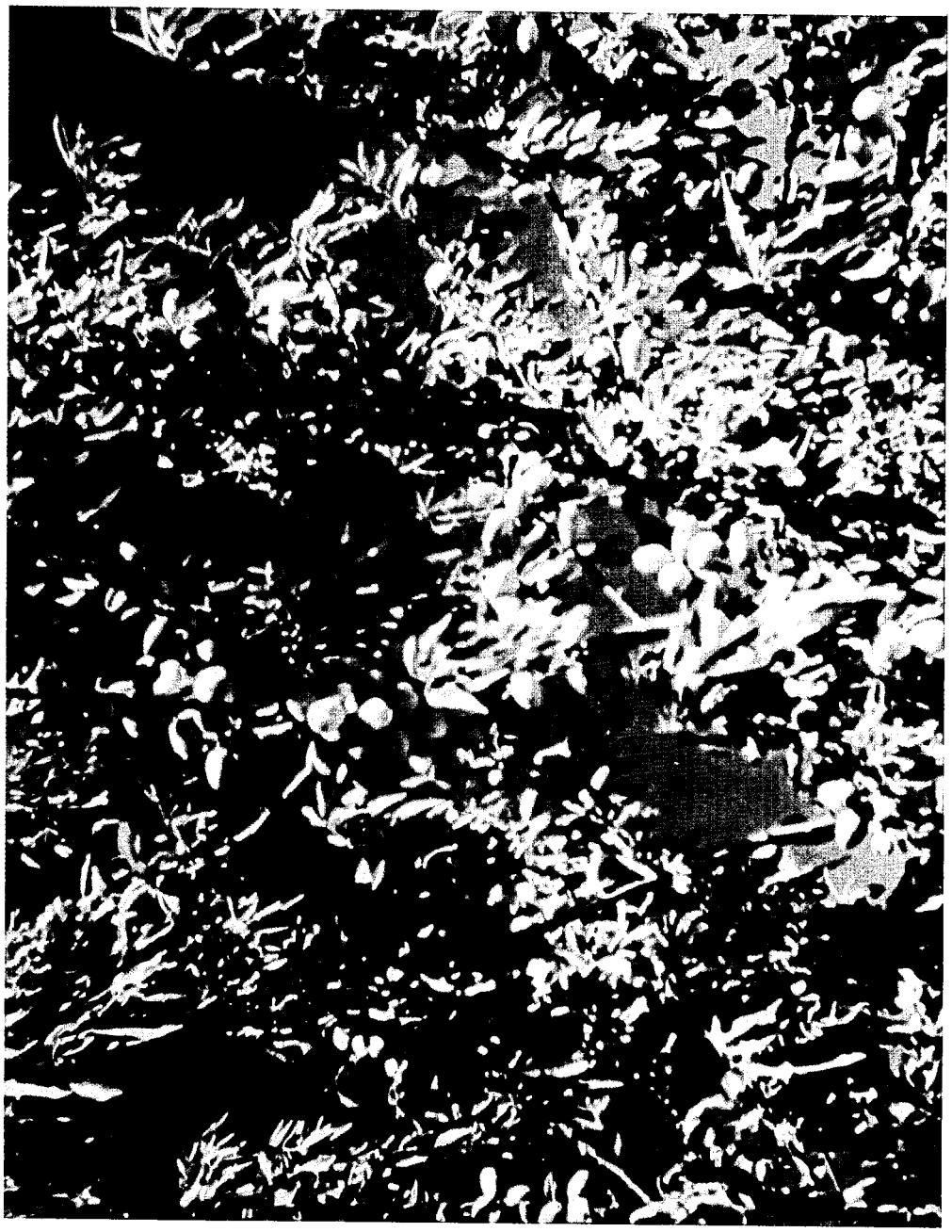

ALMOND TREE
Filed Jan. 26, 1972 3 Sheets-Sheet 2
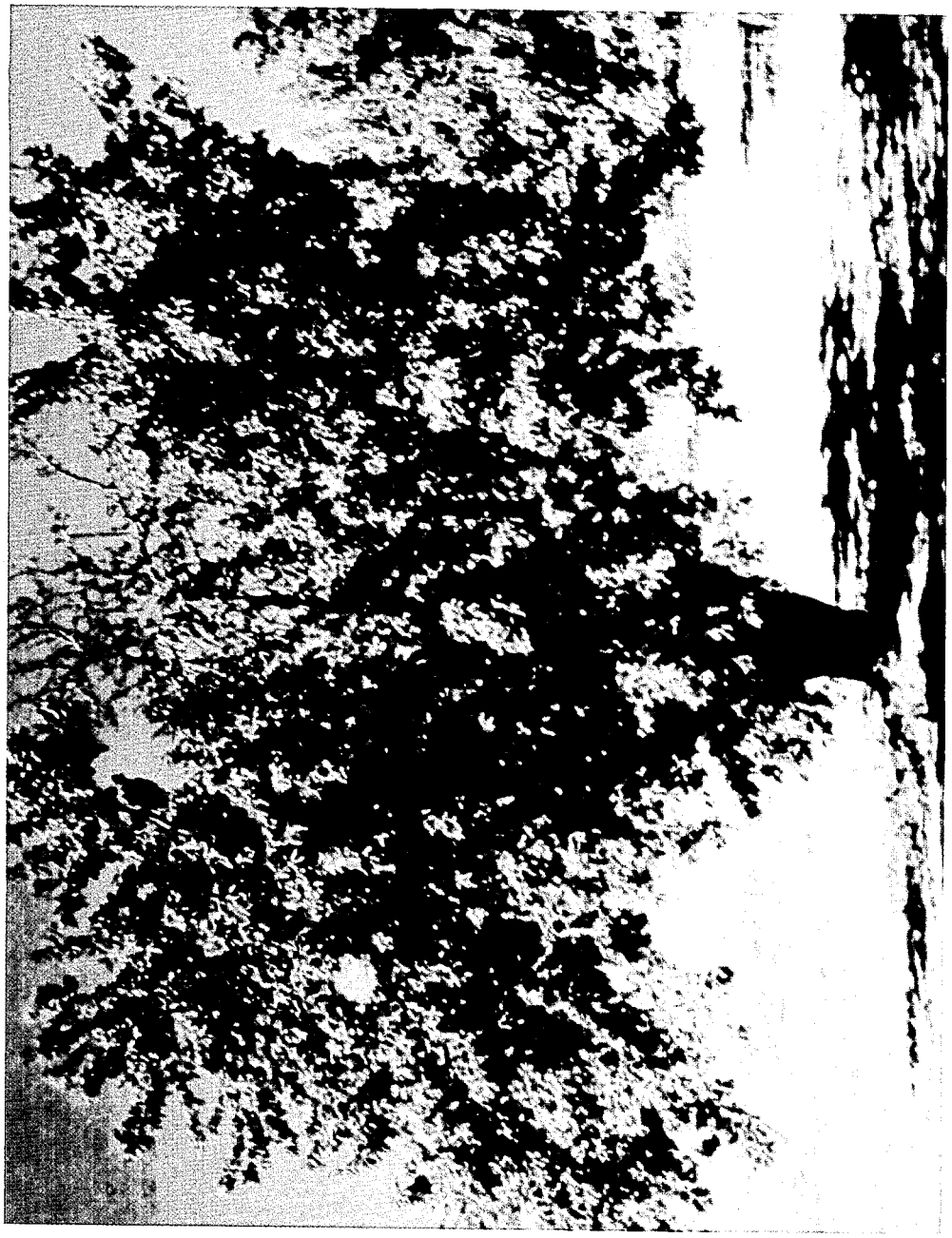

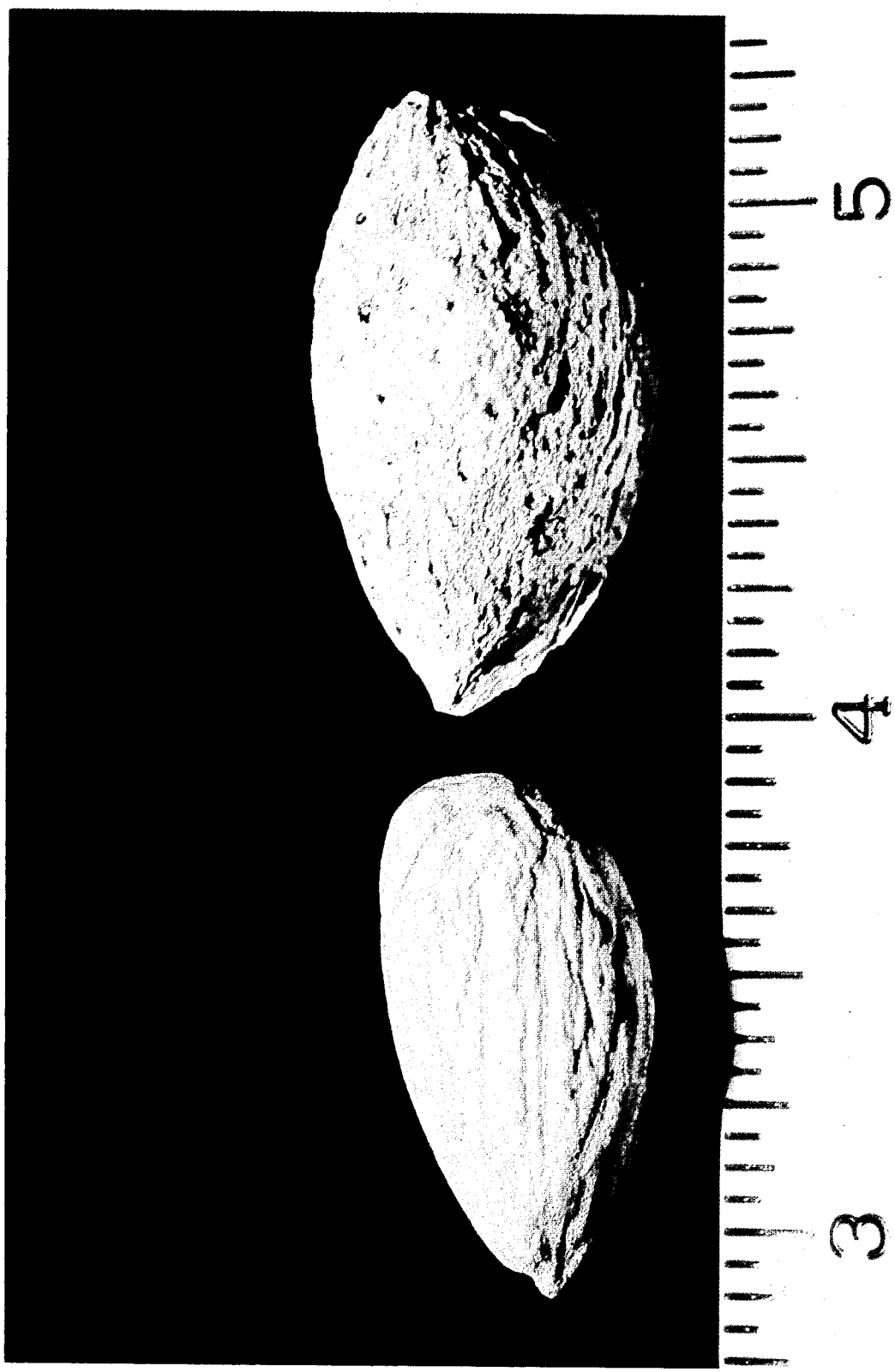
3
4
5

United States Patent Office

Plant Pat. 3,467
Patented Feb. 5, 1974

3,467

ALMOND TREE

Alfonzo Ramos Carrion, Rte. 1, Box 32,
Arbuckle, Calif. 95912

Filed Jan. 26, 1972, Ser. No. 202,709
Int. Cl. A01h *5/03*
U.S. Cl. Plt.—30 1 Claim The present variety of almond tree was discovered by me, growing as a chance seedling in a small gully, on my ranch located in Arbuckle, in the county of Colusa, State of California. After its discovery, I observed the seedling quite carefully and recognized that it was distinct from other varieties of almonds.

I asexually reproduced the present variety of almond tree by grafting, on almond and peach root stock, on my ranch located as aforesaid; such reproductions having run true to the original tree in all respects for a period of 5 years.

The herein claimed variety of almond tree in comparison to the Nonpareil (unpatented) and which is the previously known variety which resembles it most closely in general respects, is characterized, as to novelty, by:

A tree which is of medium size, vigorous and dense growth, with abundant foliage; the leaves being slightly more glossy and smaller than those of the Nonpareil.

A tree which blooms very heavily about one week before the Nonpareil, and is a very heavy producer of medium sized nuts, and having a high percentage of kernel to shell and of a form the same as the nuts of the Nonpareil; the kernels being of good quality and having much the same flavor as the Mission variety.

The instant variety is further characterized by apparently being self-pollinating and a pollinizer for Nonpareil, and having extremely high resistance to disease; these factors being evidenced, respectively, by the heavy bearing of new trees although selected portions of the bud covered by plastic preventing cross-pollinization, and by the absence of dead or diseased wood in the original and new trees, and the low rate of reject kernels from insect infestation.

The sheets of drawings show respectively, the heavy fruiting habit, a nut and kernel, and the branching habit.

The botanical details of this new and distinct variety of almond tree, with color definitions (except those in common color terms), reference to Maerz and Paul Dictionary of Color are as follows:

Tree:
- *Density.*—Very dense
- *Size.*—Medium
- *Vigor.*—Vigorous

Trunk:
- *Form.*—Stocky
- *Texture.*—Smooth

Branches:
- *Form.*—Medium
- *Texture.*—Smooth
- *Branching habits.*—Oblique

Color:
- *Wood.*—Green

Foliage:
- *Quantity.*—Abundant

Leaves:
- *Size.*—Medium; average length 3½"; average width ¾"
- *Form.*—Elliptical; obtuse tip
- *Thickness.*—Medium
- *Texture.*—Very smooth
- *Margin.*—Medium serrate
- *Petiole.*—Medium length; medium thickness
- *Glands.*—Average number—2; opposite; small; globose; green; positioned at junction of leaf and petiole
- *Stipules.*—None
- *Color.*—Top side—glossy medium green (22–L–8); underside—lighter green (22–L–6)

Bloom:
- *Amount of bloom.*—Very heavy
- *Color.*—White
- *Blooming period.*—Feb. 24, 1973–Mar. 4, 1973

Crop:
- *Bearing.*—Heavy bearer
- *Productivity.*—Very heavy
- *Distribution of nuts on tree.*—Clustered; well distributed
- *Harvest period.*—Sept. 1, 1973 as compared to Nonpareil Aug. 17, 1973
- *Tenacity.*—Hangs very well on tree, easy to harvest, very easy to hull Hull:
- *Outer surface.*—Smooth
- *Form.*—Regular as compared to Nonpareil
- *Thickness.*—Thin
- *Flesh.*—Fleshy
- *Suture.*—Pointed
- *Color.*—Light yellow-green (21–K–4), with short silvery pubescence
- *Dehiscence.*—Opens freely
- *Splitting.*—Along suture Nut:
- *Size.*—Medium. Average length, 1¼". Average width, ⅝". Average thickness, ½"
- *Form.*—Length/width—elongated; width/thickness—plump
- *Shell.*—Paper. Outer shell—intact; inner shell—hard; excellent seal
- *Color.*—Macaroon (12–H–7)
- *Pits.*—Small; numerous; shallow
- *Base.*—Ventrally oblique; dorsally oblique
- *Stem scar.*—Small; acute
- *Apex.*—Acute; sharp; prolonged at tip
- *Wing.*—Narrow; thin; tapered toward apex
- *Inner surface.*—Light colored
- *Percentage of kernel to nut.*—65%

Kernel:
- *Size.*—Large; average length 1⅛"; average width ⅜"; average thickness 5/16"
- *Form.*—Length/width—elongated; width/thickness—medium
- *Base.*—Ventrally oblique
- *Stem scar.*—Small; obtuse
- *Apex.*—Acuminate; sharp
- *Plumpness.*—Smooth
- *Pellicle.*—Thin
- *Pubescence.*—Smooth
- *Color.*—Light tan (13–L–8)
- *Number of doubles.*—4.9%
- *Flavor.*—Sweet
- *Quality.*—Good Tests:
- *Blanching.*—Identical to Nonpareil
- *Doubles.*—4.9%
- *Insect infestation.*—.1%; result of closed suture
- *Gum kernels.*—None
- *Moldy kernels.*—None
- *Waxy kernels.*—None
- *Rancid kernels.*—None
- *Blend.*—Blends with "California" classification (Davey, Thompson, Merced, Ruby, Ballico, Norman, California, Harvey, Vesta, Yosemite)

The almond tree and its nuts herein described may vary in slight detail due to climatic and soil conditions under which the variety may be grown; the present description being of the variety as grown in the Sacramento Valley of California.

I claim:

1. A new and distinct variety of almond tree characterized by good disease resistance and a well-sealed nut of good quality and flavor comparable to the Mission variety.

References Cited

UNITED STATES PATENTS

P.P. 3,046 4/1971 Wells ---------- Plants—30

ROBERT E. BAGWILL, Primary Examiner